(12) United States Patent
Guffin, III

(10) Patent No.: US 9,504,287 B1
(45) Date of Patent: Nov. 29, 2016

(54) SUSPENSION SYSTEM FOR A NEW GOGGLE FRAME PLATFORM

(71) Applicant: George Guffin, III, Jackson, MS (US)

(72) Inventor: George Guffin, III, Jackson, MS (US)

( * ) Notice: Subject to any disclaimer, the term of this patent is extended or adjusted under 35 U.S.C. 154(b) by 326 days.

(21) Appl. No.: 14/180,878

(22) Filed: Feb. 14, 2014

Related U.S. Application Data

(60) Provisional application No. 61/765,353, filed on Feb. 15, 2013.

(51) Int. Cl.
*A42B 3/18* (2006.01)

(52) U.S. Cl.
CPC .................................. *A42B 3/185* (2013.01)

(58) Field of Classification Search
CPC ...................................................... A42B 3/185
USPC .......... 2/6.3, 6.5, 6.7, 15, 422; 128/857, 858
See application file for complete search history.

(56) References Cited

U.S. PATENT DOCUMENTS

| | | | |
|---|---|---|---|
| 2,368,303 A | 1/1945 | Johnston | |
| 3,262,125 A | 7/1966 | Bowen | |
| 3,931,646 A | 1/1976 | Loughner | |
| 4,653,124 A * | 3/1987 | McNeal | A61F 9/029 128/206.21 |
| 4,686,712 A | 8/1987 | Spiva | |
| 4,918,753 A | 4/1990 | Mermillod | |
| 5,666,663 A | 9/1997 | Bolle | |
| 5,987,652 A | 11/1999 | Fowler | |
| 6,694,530 B2 | 2/2004 | Maloney | |
| 6,732,383 B2 | 5/2004 | Cleary et al. | |
| 6,912,727 B2 * | 7/2005 | Buchanan, Jr. | G02B 7/002 2/414 |
| 7,003,802 B2 | 2/2006 | Broersma | |
| 7,168,095 B2 | 1/2007 | Wright | |
| D548,251 S | 8/2007 | Broersma | |
| 7,343,631 B2 | 3/2008 | Lin | |
| 7,617,544 B2 | 11/2009 | Hahn et al. | |
| 7,681,257 B1 | 3/2010 | Broersma | |
| 8,011,026 B2 | 9/2011 | Stevens | |
| 8,028,344 B2 | 10/2011 | Rogers et al. | |
| D658,814 S | 5/2012 | Wirtz et al. | |
| 8,225,431 B2 * | 7/2012 | Cyr | A42B 3/22 2/15 |
| D669,113 S | 10/2012 | Sandor et al. | |
| 8,327,466 B2 | 12/2012 | Hahn et al. | |
| 8,549,672 B2 | 10/2013 | Stevens | |
| 8,661,562 B2 | 3/2014 | Calilung | |
| 2002/0104153 A1 | 8/2002 | Benedict et al. | |
| 2003/0101507 A1 | 6/2003 | Cleary et al. | |
| 2004/0143879 A1 | 7/2004 | Robertson | |
| 2005/0183190 A1 | 8/2005 | Hussey | |

(Continued)

FOREIGN PATENT DOCUMENTS

WO        2011035071 A1        3/2011

*Primary Examiner* — Katherine Moran

(74) *Attorney, Agent, or Firm* — Garvey, Smith, Nehrbass & North, L.L.C.; Seth M. Nehrbass; Mackenzie D. Rodriguez

(57) ABSTRACT

A head and eye protection apparatus for use in conjunction with a helmet that envelops a wearer's head, the helmet having a front opening that enables the wearer to see. The helmet has upper and side edges that surround the front opening. A goggle provides a transparent viewing lens supported by a peripheral frame. The frame includes an upper frame section, left and right side frame sections and a lower frame section. The goggle frame is suspended via a dual suspension system wherein a first apparatus seats the goggle frame to the helmet, and a second apparatus seats the goggle frame to the user's face.

17 Claims, 20 Drawing Sheets

(56) References Cited

U.S. PATENT DOCUMENTS

| | | |
|---|---|---|
| 2006/0000011 A1 | 1/2006 | Reichow et al. |
| 2006/0179554 A1 | 8/2006 | Barton |
| 2008/0155736 A1 | 7/2008 | Paulson |
| 2008/0301858 A1 | 12/2008 | Wang-Lee |
| 2008/0313792 A1 | 12/2008 | Pino |
| 2009/0038057 A1 | 2/2009 | Tews |
| 2010/0064405 A1* | 3/2010 | McGovern ............... F41H 1/04 2/6.7 |

* cited by examiner

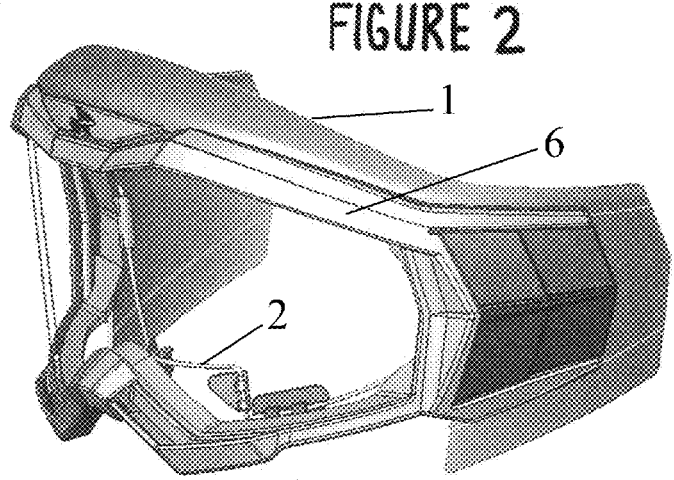
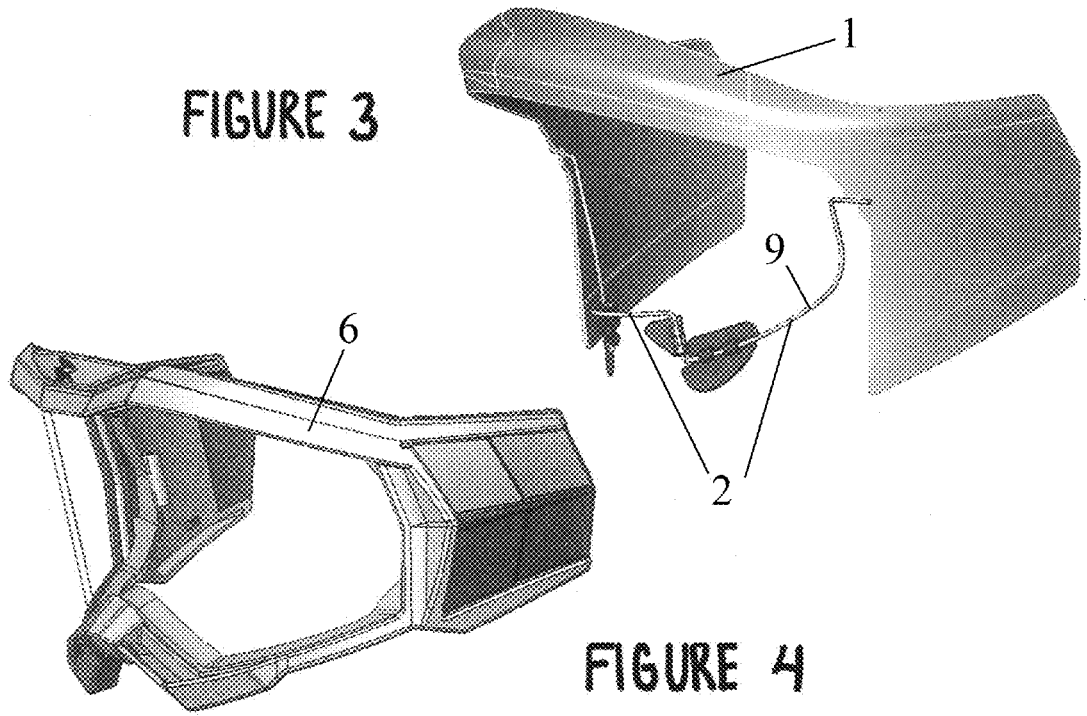

SUSPENSION SYSTEM FOR A NEW GOGGLE FRAME PLATFORM

CROSS-REFERENCE TO RELATED APPLICATIONS

This application claims priority to U.S. Provisional Patent Application No. 61/765,353 filed Feb. 15, 2013, the entirety of which is hereby incorporated by reference for all purposes.

Incorporated herein by reference are my:
U.S. Provisional Patent Application Ser. No. 61/298,075, filed 25 Jan. 2010;
U.S. patent application Ser. No. 12/048,494, filed 14 Mar. 2008;
U.S. Provisional Patent Application Ser. No. 60/894,800, filed 14 Mar. 2007,
U.S. patent application Ser. No. 11/532,627, filed 18 Sep. 2006; and
U.S. Provisional Patent Application Ser. No. 60/749,888, filed 12 Dec. 2005. However,
this is not a divisional, continuation, or continuation-in-part of any patent application.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to head wear/eye protection namely helmets and goggles. More particularly the present invention relates to improved head and eye protection in which novel apparatuses are attached to a new platform "goggle frame" that is used in conjunction with a helmet that envelopes a wearer's head. The current invention also includes any type of eyewear that these innovations may apply to with or without the use of protective headwear.

2. General Background of the Invention

Motorcycle riders typically wear a helmet that has a wind screen or face shield of some sort. These types of head gear or head wear vary depending upon the type of motorcycle or use thereof. There are basically two types of motorcycles. The most common type is a road version which spends most of its time on paved highways, streets, parking lots and the like. A second type of motorcycle is an off-road machine that is used to traverse the back country. These off-road machines are configured to carry a rider through forests, fields, mountains and deserts. Such environments can be dirty and dusty. For this reason, many off-road motorcycle riders prefer to wear goggles instead of a face shield. However, goggles suffer in that they can severely restrict the field of view of the wearer.

Typically, a motorcycle helmet has a forward viewing opening that is bordered by an upper edge of the helmet and a pair of side edges. These edges surround the forward viewing opening and provide the only area that is available for the placement of goggles. Goggles are typically small and thus restrict the user's field of vision. They are necessary for providing a seal against dirt and dust, especially when off road. Goggles are commonly used by off-road motorcycle riders to protect the eyes from dust, dirt, debris, etc.

Current modern goggle base structure has not changed since its first inception. Basically it is a foam wrapped frame placed around the face with a lens and venting. Its major limitation is the interior structural parameter of the facial opening of the helmet. This limited space has stifled any new development of the modern goggle frame to design and build on. The current invention will allow for a new goggle frame platform for designing a multitude of innovative components for the head/eye protection industry.

There have been many attempts to solve the issues attributed to the modern goggle. These relate to fit, comfort, ventilation, air filtration, heat, cold, environmental elements (water, mud, snow, dust, sand, rocks, dirt, etc.), vision, and other issues that may affect the goggle. Some have been successful due to advancements in material technology and others were limited to the parameters. The parameters set for the modern goggle has stifled its ability to evolve and create new designs solutions for the issues attributed to it. The current modern goggle has become a billboard for cosmetic style and graphic design exercises. The current modern goggle frame has reached its limit.

Being able to provide a new frame platform via the current invention opens endless design possibilities for new solutions and can even revive old ones that were not possible until now.

The present invention replaces the parameters of the modern goggle with new parameters allowing endless design possibilities for the new frame platform. This current invention provides the next step in the evolution of the goggle. The next generation goggle will be a true example of Form follows Function.

Some goggle arrangements have been patented. The following possibly relevant US Patents and US Patent Applications are incorporated herein by reference:
U.S. Pat. Nos. 3,262,125, 4,686,712, 4,918,753, 5,666,663, 5,987,652, 6,694,530, 6,732,383, U.S. Patent Application Nos. 2002/0104153, 2003/0101507, 2004/0143879.

U.S. Pat. Nos. 4,686,712; 4,918,753; and 6,694,530 disclose goggles for a motorcycle helmet where the goggles attach in some way directly to the helmet.

U.S. Pat. Nos. 3,262,125; 5,987,652; and US Publication No. 2004/0143879 disclose helmets with attached goggle arrangements.

U.S. Pat. No. 6,732,383 and US Publication No. 2003/0101507 disclose goggles designed to be worn with a helmet.

BRIEF SUMMARY OF THE INVENTION

The goggle of the present invention is a hybrid construction that uses in part the helmet and in part the user's face for an enlarged viewing area while providing a complete fit. Once a user adorns a helmet it becomes one with the user's head. The goggle of the present invention is designed to integrate with both the helmet and the face of the user.

The present invention provides eyewear placed on the face with a lens material (e.g. a safety lens such as polycarbonate) to protect the eyes from dirt and debris. The eyewear of the present invention is a design that integrates helmet, lens and face to protect the user's eyes and seal out dust.

The present invention thus provides a head and eye protection apparatus for a motorcycle rider or like user.

The current invention is a suspension system composed of two apparatuses. The first apparatus is one that seats the goggle frame to the helmet. The second apparatus seats the goggle frame to the user's face. The first apparatus suspends the goggle frame from the helmet enabling the goggle frame to absorb vibrations during use while keeping the goggle safely seated to the helmet. The second apparatus suspends the goggle frame from the user's face enabling the goggle frame to absorb vibrations during use while keeping the goggle safely seated to the user's face.

The current invention enables new advancements in goggle design by providing a pair of apparatuses "suspension systems" for a new platform "goggle frame". This new platform provides a design base for solving existing problems with the current modern goggle. These solutions and or innovations include air management, aerodynamics, visual enhancements, electronic applications, protection from environmental elements and comfort.

The current invention is the solution to how the goggle frame reacts to organic and inorganic surfaces. The helmet being inorganic with its engineered variations of designs and the infinite organic characteristics of the human face together produced a design that merges the organic and inorganic. This merger is a cohesive functional solution where form follows function. Prior attempts have failed because they did not take into consideration the organic and inorganic properties of each entity. The helmet and human face were treated as one.

The present invention's main purpose is to allow the new platform "goggle frame" to be safely secured to the helmet and user's face. This provides the frame a secure venue to implement its designed safety features for eye protection. These eye safety features include but are not limited to the lens, venting, and sealing. With different helmet and human characteristics the current invention provides the new platform "goggle frame" the ability to move beyond the current boundaries and explore new designs in air management, aerodynamics, visual enhancements, electronic applications, protection from environmental elements and comfort.

The current invention includes two apparatuses with four components. Each of the four components when working in conjunction with each other provides a safe, secure, functional and quality fit. The four components are the silicone suspension, wire face flange, face flange paddles and the flexible material. The current invention is the latest evolution for goggle design. When the current invention's apparatuses and components are working in conjunction with each other they provide the goggle with a higher level of eye safety and protection. By allowing the parameters to expand beyond the limitations of the modern goggle frame new and improved designs can evolve.

The present invention includes a flexible multidirectional face flange.

An optional exhaust system for the goggle apparatus of the present invention can be provided. Such an exhaust system employs one or more exhaust ports to vent the inside air to the outside, bypassing the facial opening of the helmet. This optional exhaust system can be composed of a series of exhaust ports that can be located anywhere around the side and/or top of the goggle frame. These exhaust ports remove the air that is received as the rider moves forward. The forward motion pushes air into the intake vents where it moves into the interior of the goggle. As air pressure builds up the air is forced into the opening of the exhaust port. This opening channels air to the outside, bypassing the facial opening.

The exiting exhaust air leaves through the exhaust port at a rear facing opening that allows air to merge into sequence with the mass air flow passing around the helmet. Each rear exhaust port provides an exit for the exhaust air to merge into a sequence with the mass air flow that is passing around the user's helmet. This exhaust system is part of a three part system to vent goggles. The first is air intake, the second is pressurized interior air, the third is the exhaust port system that sends the interior air out of the goggle in a sequence with the mass air flow. This three part system can be described as a venturi effect. The air intake vents can be covered with particulate porous foam to filter dirt or other particulate matter.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 2 shows the current invention attached to a platform goggle frame;

FIG. 3 shows the current invention unattached to the platform goggle frame;

FIG. 4 shows the platform goggle frame minus the current invention;

DETAILED DESCRIPTION OF THE INVENTION

Figure 1:
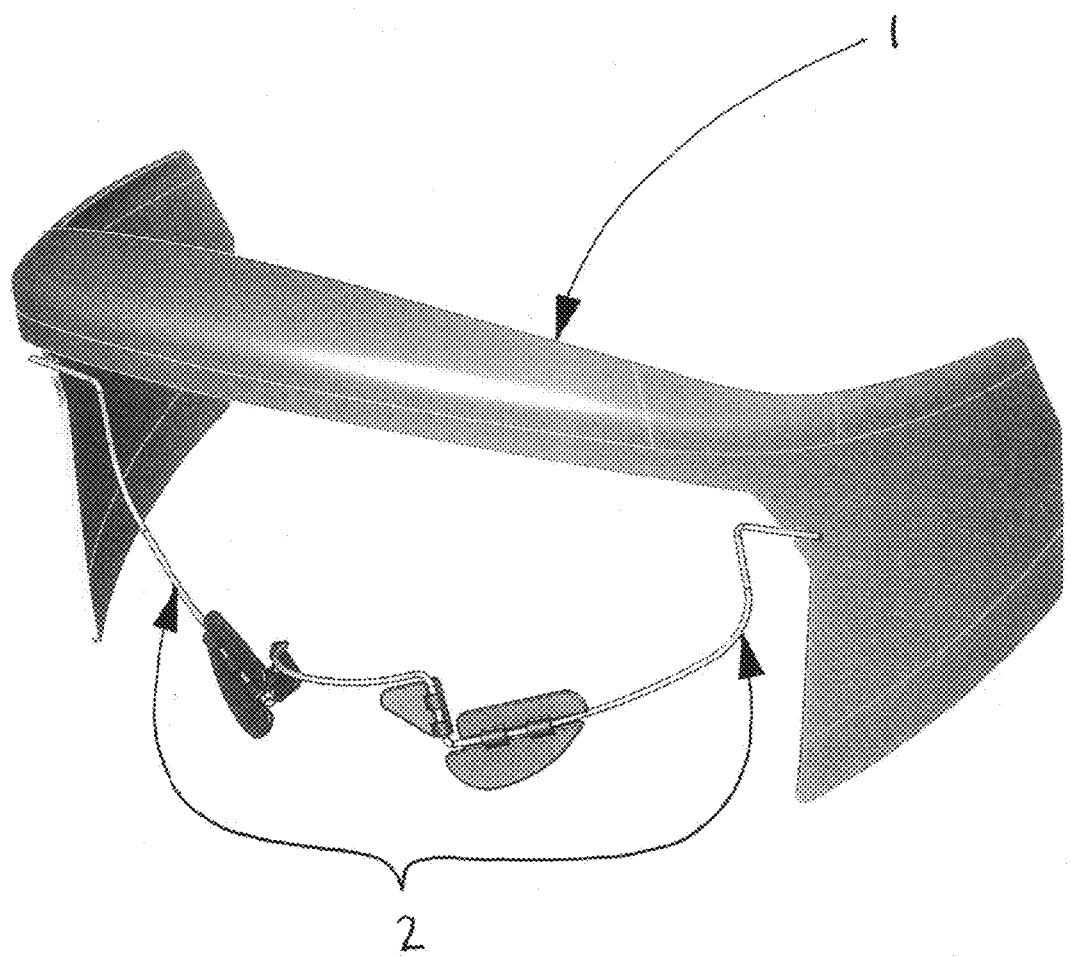
FIG. 1 is a view of the current invention showing a two apparatus system.
Figure 5:
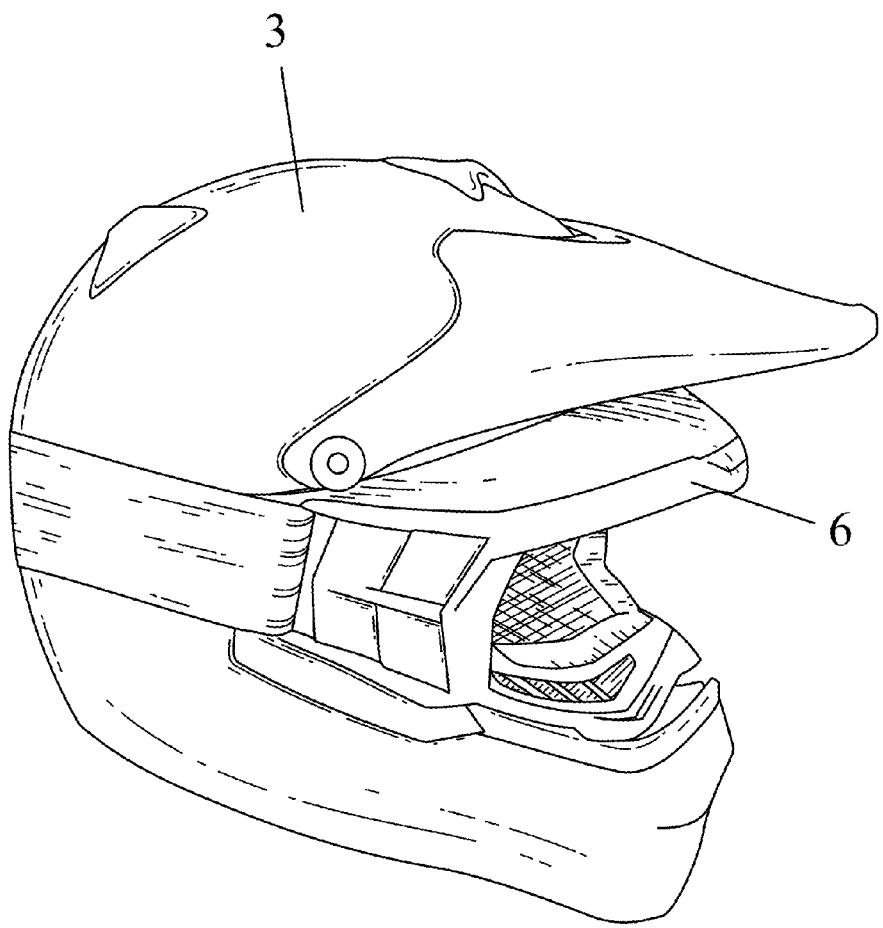
FIG. 5 shows the current invention in use with the platform goggle frame and helmet.
Figure 6:
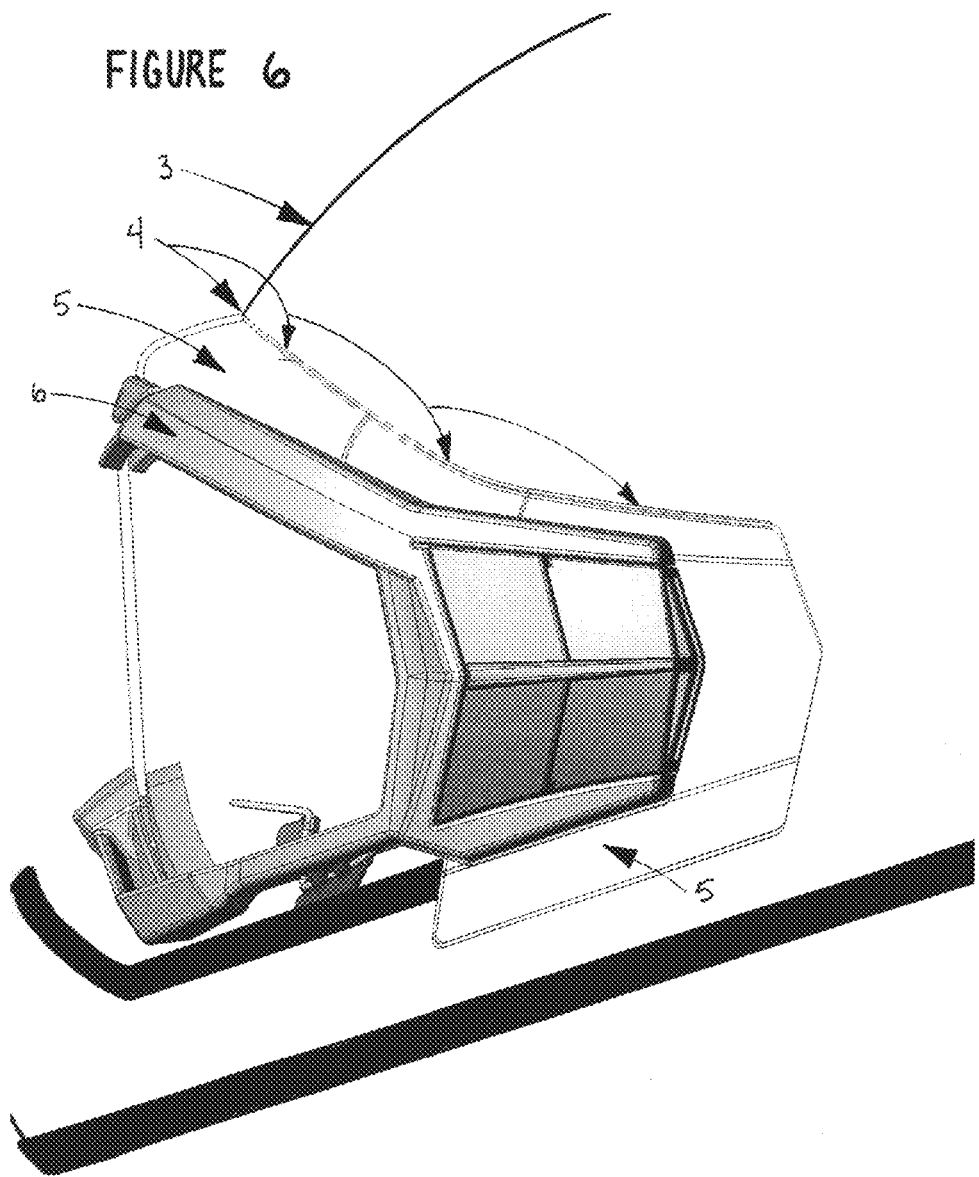
FIG. 6 is a side view of a preferred embodiment of the present invention, showing the silicone suspension attached to a new platform goggle frame, and the silicone suspension's leading edge as it relates to the outer shell of the helmet.
Figure 7:
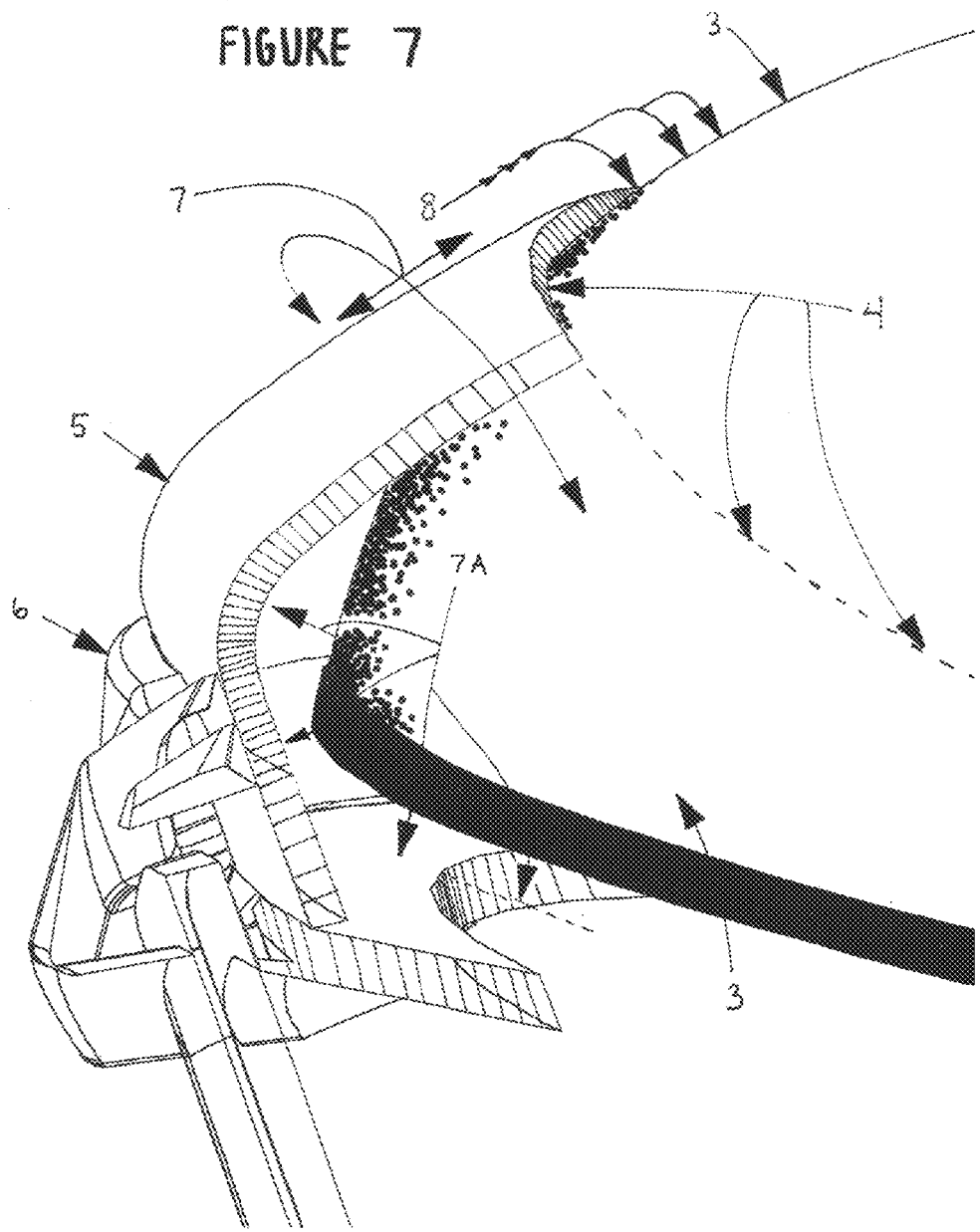
FIG. 7 is a top view of a preferred embodiment of the present invention, showing the silicone suspension's fit range as it relates to the new platform goggle frame and the exterior shell of the helmet, and the silicone suspension's compression range as it relates to the new platform goggle frame and the exterior shell of the helmet.
Figure 8:
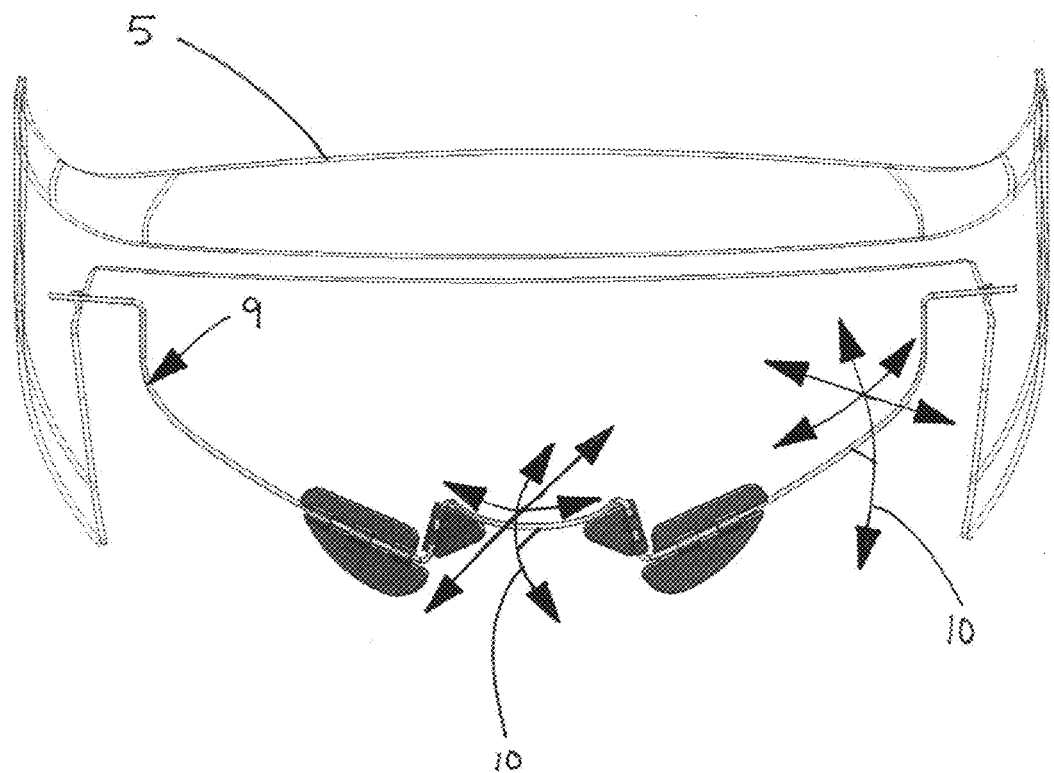
FIG. 8 shows the multidirectional movement of the wire face flange.
Figure 9:
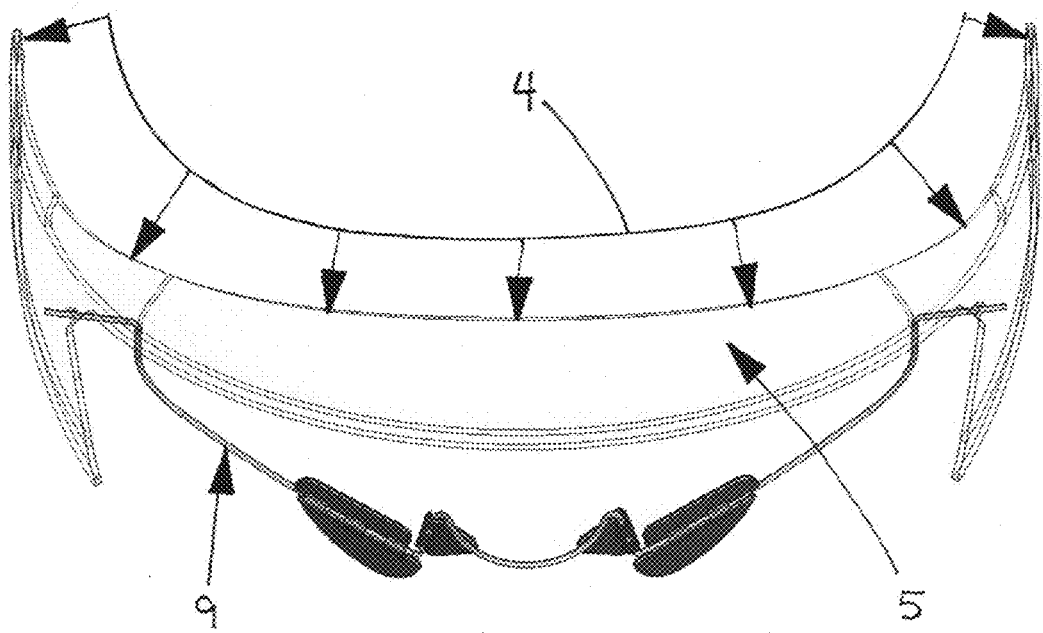
FIG. 9 shows the silicone suspension's leading edge that is first to engage with the exterior shell of the helmet.
Figure 10:
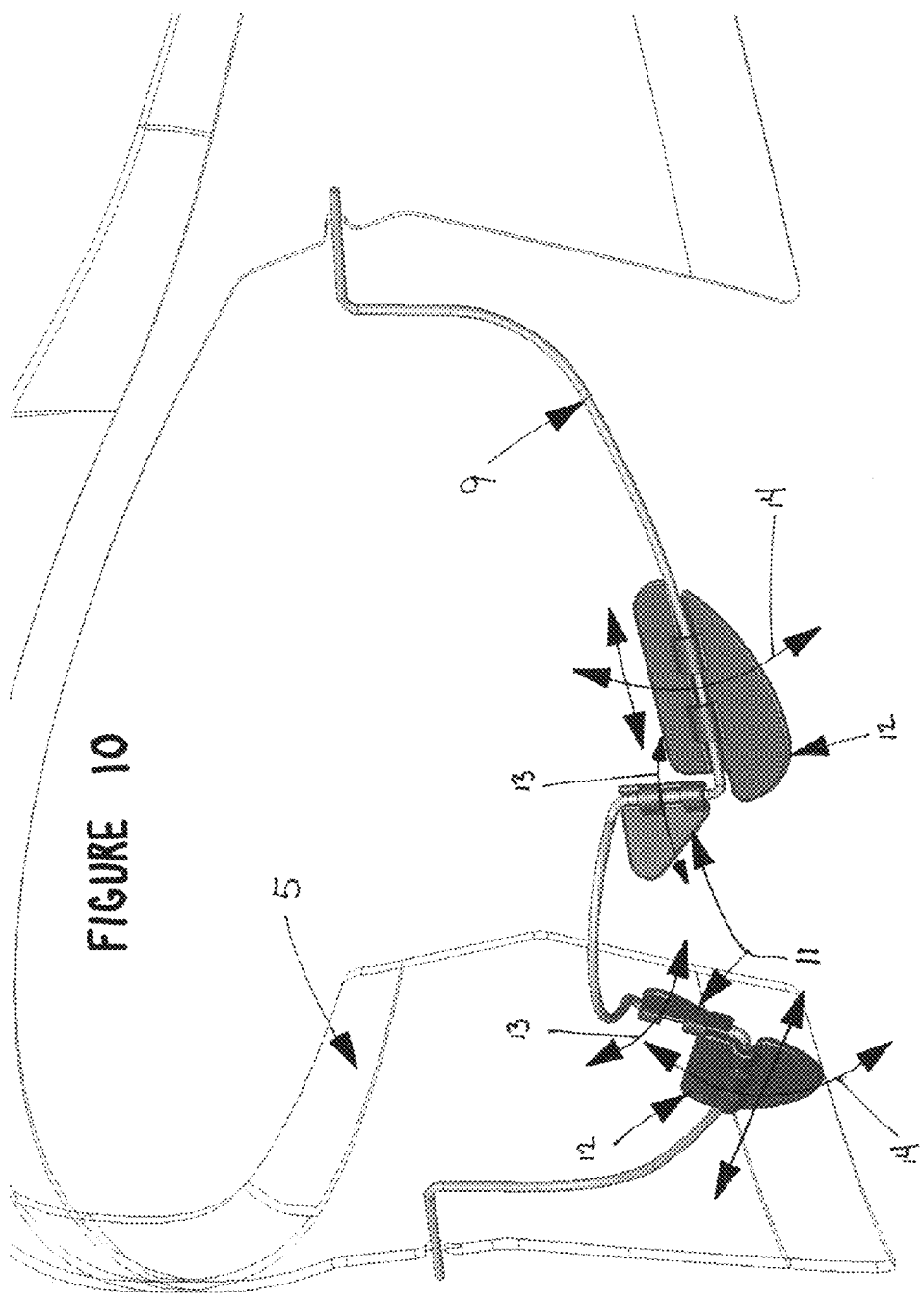
FIG. 10 shows the movement direction of the nose and cheek paddles as they are attached to the wire face flange.
Figure 11:
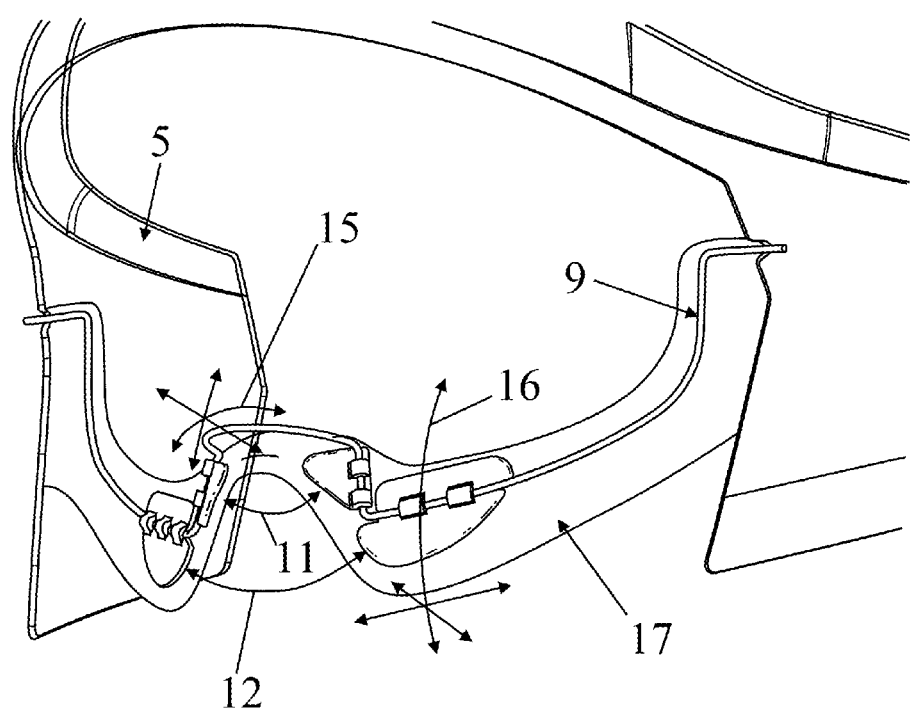
FIG. 11 shows the multidirectional movement of the face flange stretchable material.
Figure 12:
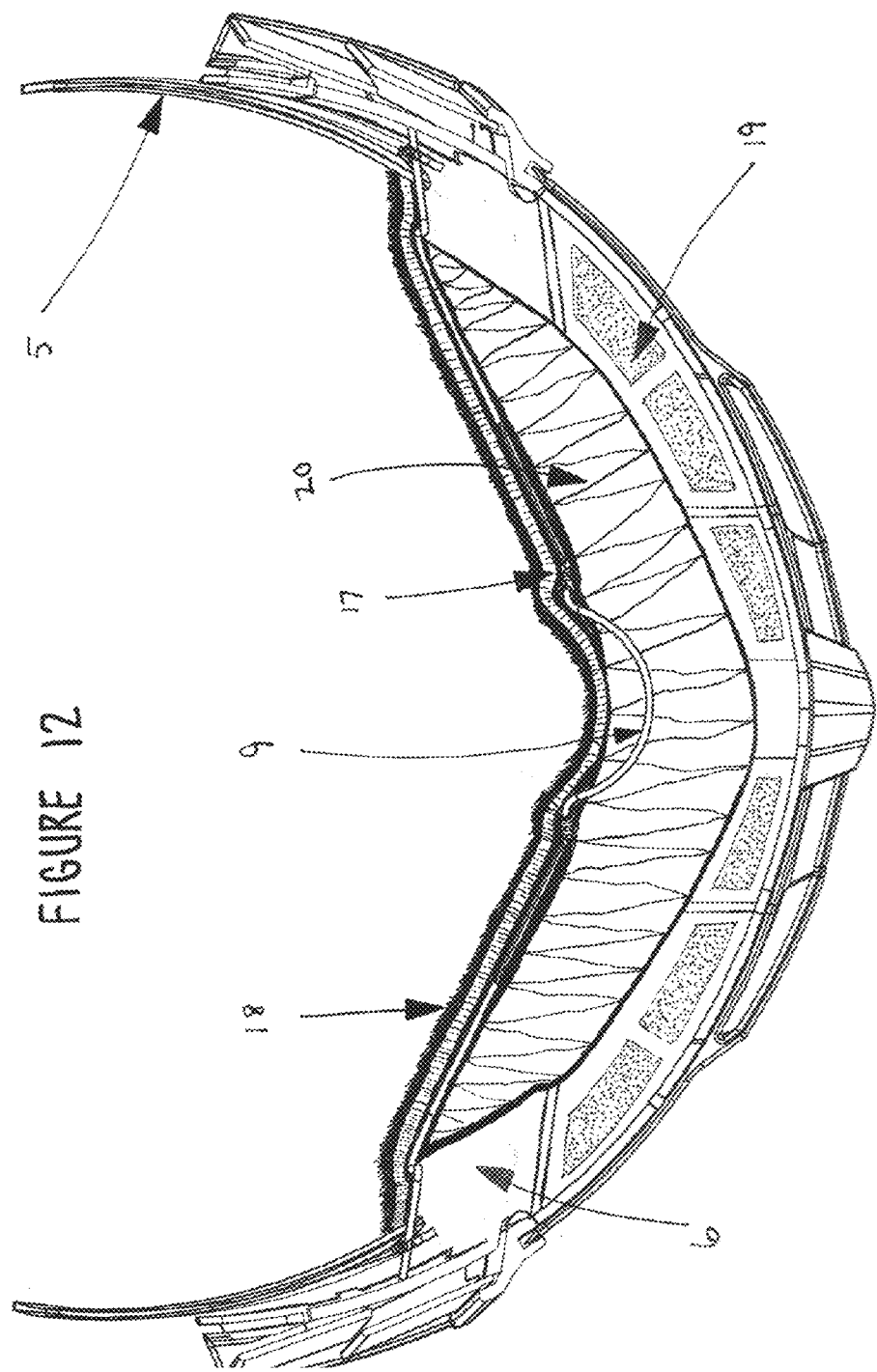
FIG. 12 is a top view of a preferred embodiment of the present inventions, showing the face flange with attached stretchable facial material as it relates to the wire face flange, and the stretchable interior seal material as it relates to the face flange's stretchable material and new platform goggle frame.
Figure 13:
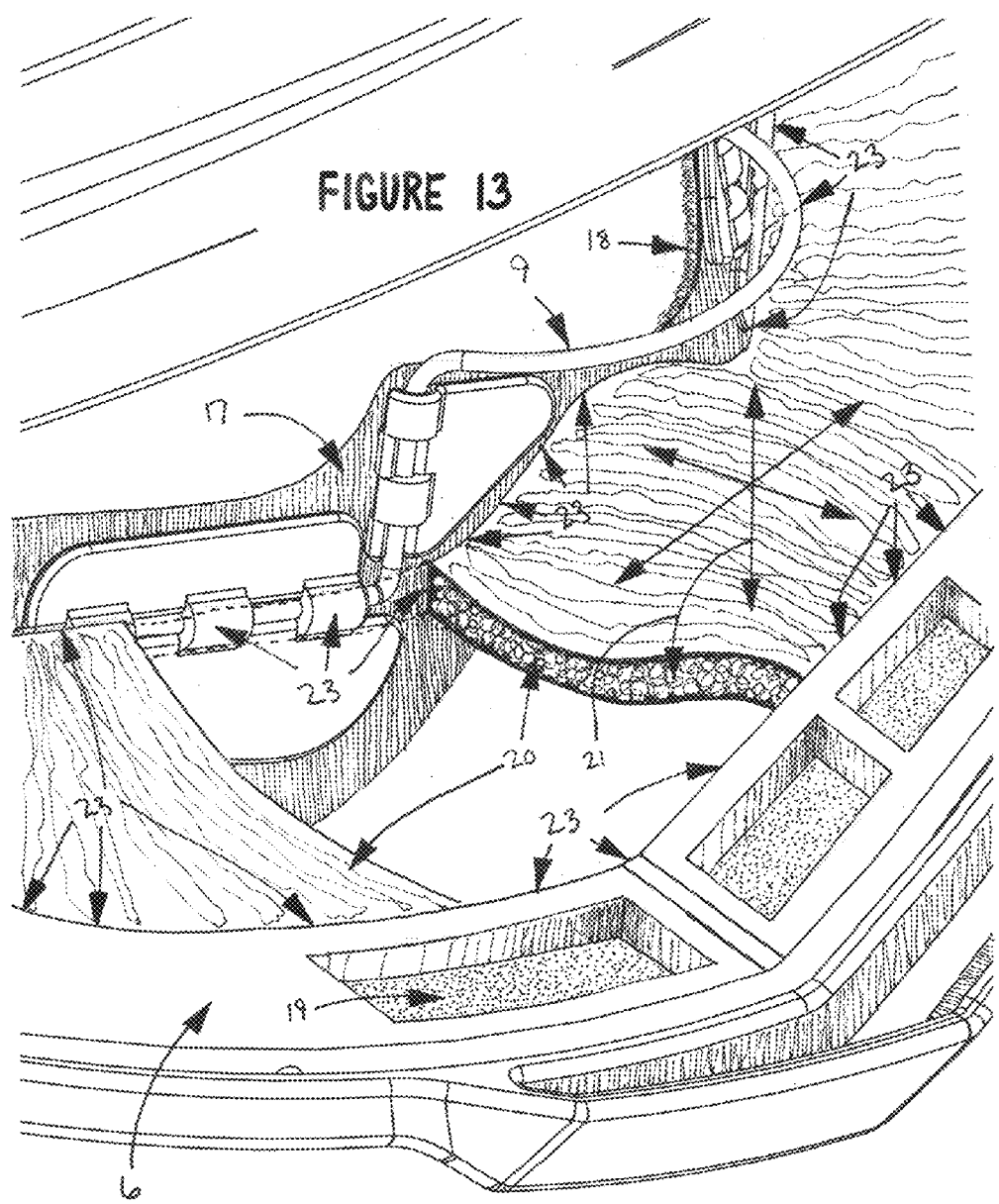
FIG. 13 shows the multidirectional movement and attachment locations of the stretchable interior seal material.
Figure 14:
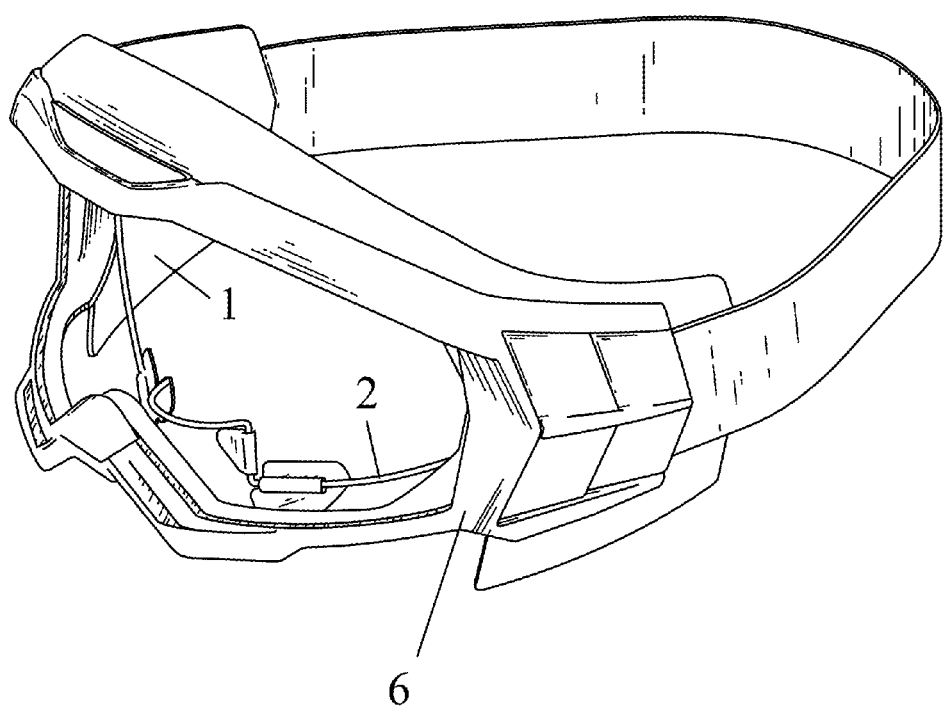
FIG. 14 is a prototype of an embodiment of the current invention without vents or flexible material.
Figure 15:
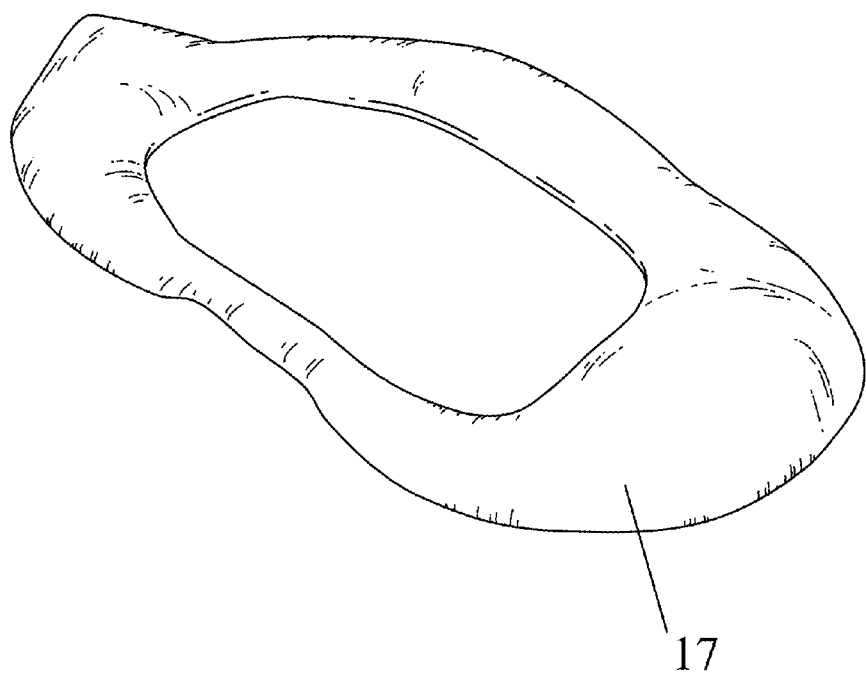
FIG. 15 is a back view of the face flange flexible material of the preferred embodiment of the present invention, showing flexible material for covering the nose and cheeks, and sealing foam for attaching to the temple areas.
Figure 16:
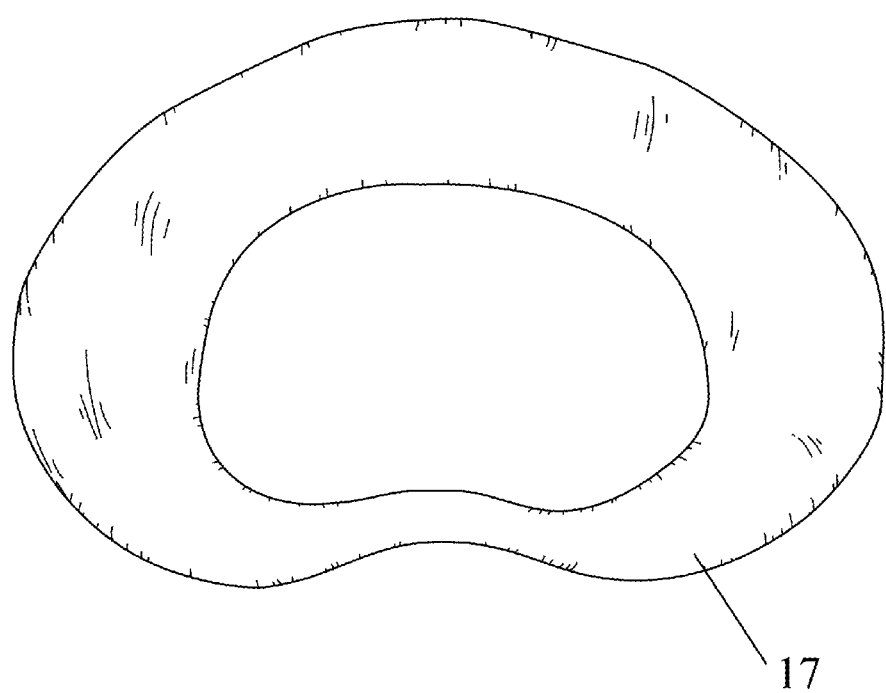
FIG. 16 is a front view of the face flange flexible material of the preferred embodiment of the present invention, showing the Velcro-compatible fabric cover.
Figure 17:
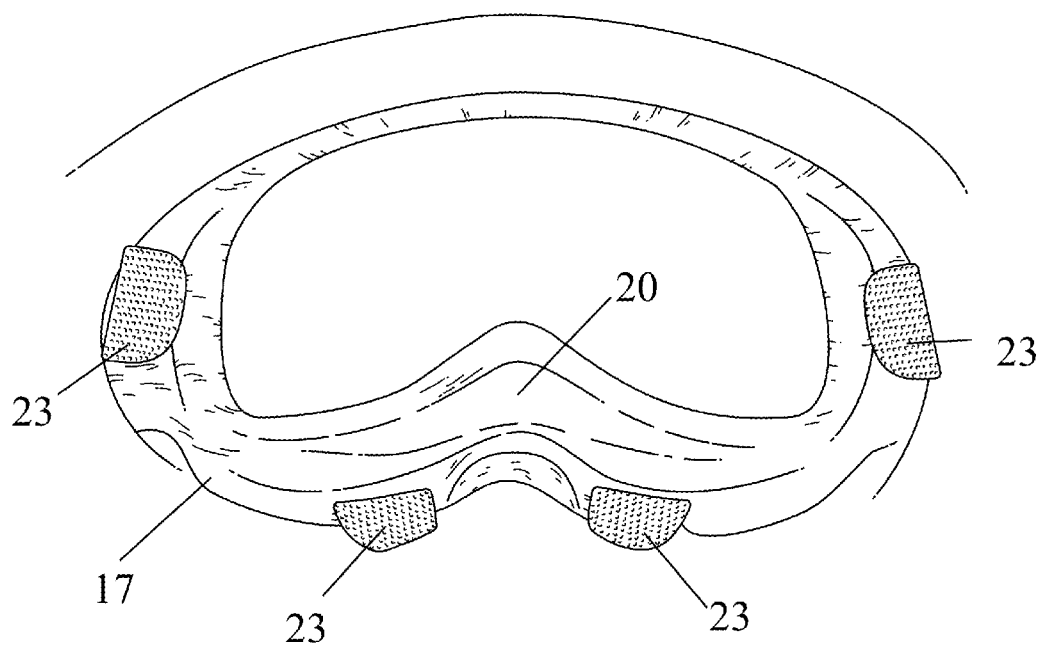
FIG. 17 is an interior view of the preferred embodiment of the present invention, showing Velcro sections for attachment to the front side of the face flange flexible material.
Figure 18:
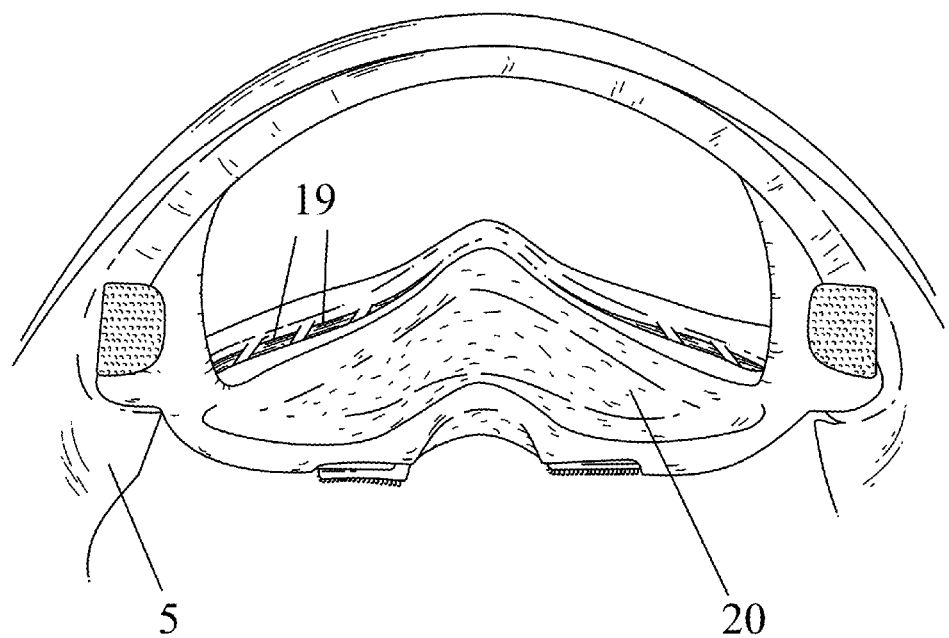
FIG. 18 is an interior view of the preferred embodiment of the present invention, without the platform goggle.
Figure 19:
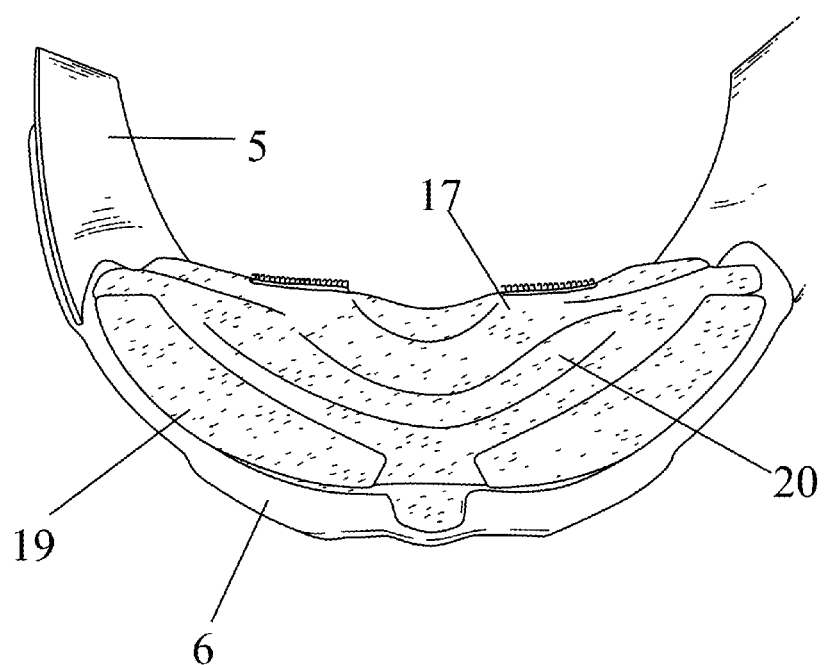
FIG. 19 is a bottom view of the preferred embodiment of the present invention, without the platform goggle.
Figure 20:
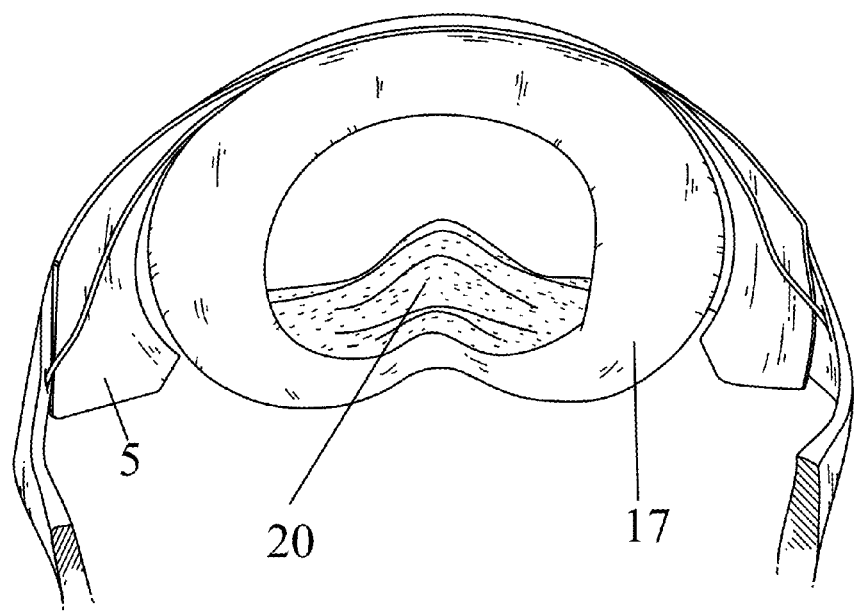
FIG. 20 is an interior view of the preferred embodiment of the present invention, without the platform goggle.
Figure 21:
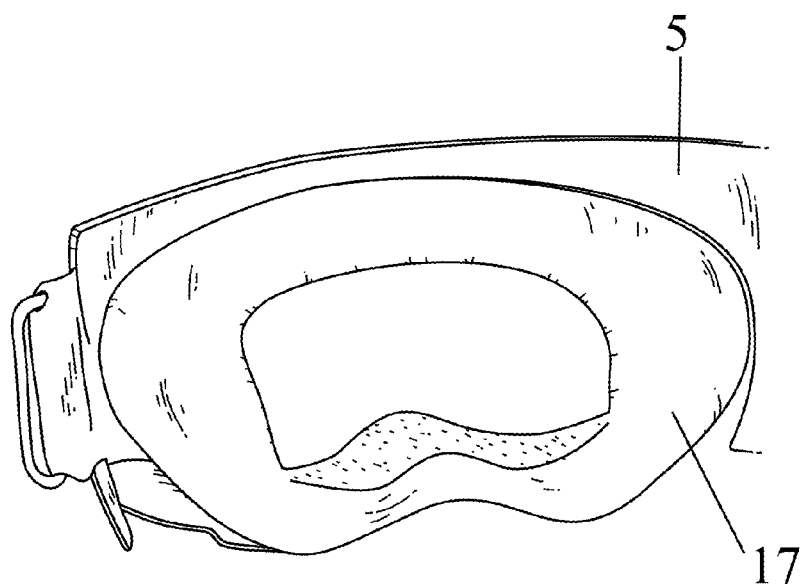
FIG. 21 is an interior view of the preferred embodiment of the present invention, without the platform goggle; and, FIG. 22 is an exterior view of the preferred embodiment of the present invention, without the platform goggle.
Figure 22:
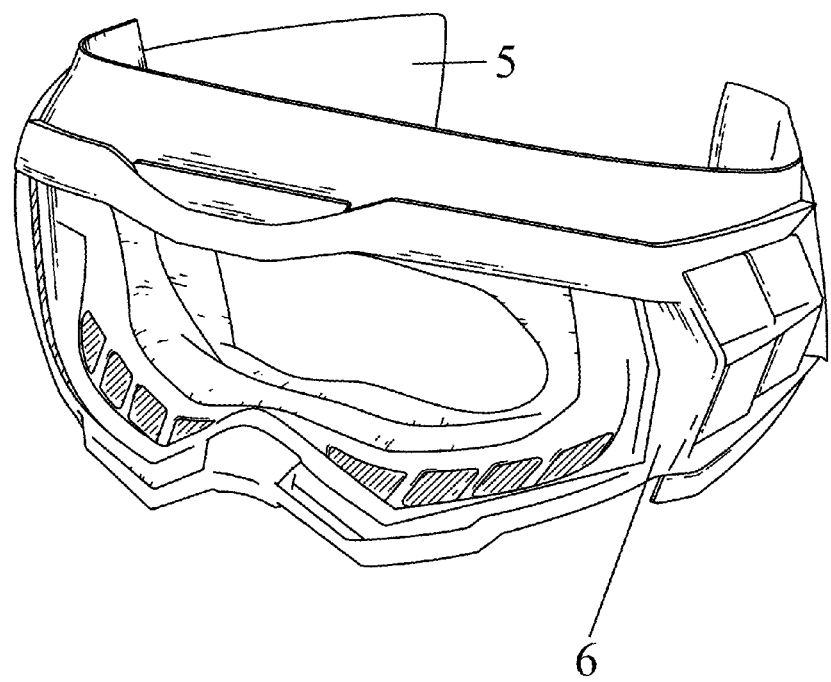

FIG. 1 shows the two apparatuses of a preferred embodiment of the present invention. Apparatus 1 is a suspension system that attaches to a goggle frame allowing the frame to suspend the goggle between its frame and to the exterior shell of a helmet while providing a safe and secure seal. Apparatus 2 is a suspension system that attaches to a goggle frame allowing the frame to suspend the goggle between its frame and the face of the user while providing a safe and secure seal.

The silicone suspension 1 attaches to the new platform "goggle frame." This is part of the suspension system between the goggle frame and outer shell of the helmet. This suspension system is not applicable to today's modern goggle frame.

This silicone suspension 1 is a load bearing structure that suspends the goggle frame from the helmet. Without this structure the goggle would not function with the helmet. Prior art has a goggle frame designed to fit around the facial opening of a helmet. This prior art goggle's frame lacks the ability to keep the goggle safe and secure to the helmet and user's face as the helmet and head move about during use. The silicone suspension 1 is flexible in extreme temperature providing a secure fit with shock absorbing capabilities keeping the goggle frame in a constant seated position. The silicone suspension 1 delivers a secure grip in a wide range of temperatures no matter what time of year it is used. This design upon initial engagement with the helmet allows the silicone suspension's leading edge to seal onto the outer curvature of the helmet's shell. This initial engagement is preferably such that it not only seals, it provides the goggle frame an ability to float between the outer helmet shell and the frame. A silicone gasket acts as a cushion or buffer between the hard goggle frame and the hard outer shell of the helmet. This will reduce the vibration and movement of the goggle frame as the user rides the motorcycle over rough terrain. The silicone suspension has adjustment flexibility as to where the initial engagement is made. Preferably, the user can place the goggle on the helmet in numerous locations based on personal preference. The goggle can be attached closer to the helmet's surface by compressing the silicone suspension allowing the user to seat the leading edge closer in, based on personal preferences and facial features. Preferably, the user may locate the silicone suspension's leading edge up or down to numerous locations on the outer shell of the helmet based on personal preferences and facial characteristics. This is so that no matter what the characteristics are of the user's face the silicone suspension system will be able compress and seat the leading edge up or down on the helmet's outer surface. This provides the adjustability needed to fit the individual user's facial characteristics.

Another attribute of the silicone suspension system is that it prevents environmental elements from entering the interior of the goggle from the outer shell. This is a safety feature that the modern goggle cannot do. The silicone suspension system prevents sand, dust, dirt, snow, water, mud, etc. from entering the goggle interior and affecting the user's vision. The modern goggle cannot prevent these things from happening due to the use of reticulated foam air filter and seal. The modern goggle by design fits into the facial opening of a helmet leaving a gap around the opening where sand, dust, dirt, snow, water, mud, etc. enter and make their way through the reticulated foam air filter and seal. The modern goggle reticulated foam air filter and seal can handle only so much of the environmental elements until it becomes saturated and useless. The current invention with its silicone suspension system eliminates the exposure of sealing foam to the environmental elements such as mud, water, snow, etc., that renders the goggle useless.

The second component is a wire designed face flange 2. This is part of the suspension system that is between the goggle frame and user's face. Unlike the modern goggle's face flange that's integrated into the frame creating one solid structure supporting all the goggle's components, the wire face flange 2 of current invention acts in conjunction with the goggle frame. This has the frame being the primary structure responsible for supporting all goggle components. Conversely, the modern goggle face flange has a stationary nose design structure integrated into the frame. The nose design structure of the prior art is also used to orientate the goggle to the face. The integrated urethane face flange 2 and frame of the present invention is designed to accommodate as many faces as possible. The frame of the present invention preferably uses reticulated foam for sealing the perimeter of the goggle, preventing environmental elements from getting inside the goggle and irritating the eyes. This foam compresses to form around and fill the gaps associated with different facial characteristics as it seals around the face.

The wire face flange 2 is designed to act independently with the goggle frame. This will allow for the user's head to move independently of the goggle frame without losing the stretchable materials secure seal to the face provided by the wire. The wire face flange 2 is preferably made of Nitinol. Nitinol is a medical grade wire with attributes like flexibility, strength, ability to hold shape when formed, fatigue resistance, biologically compatible and applicable range of tension. The wire face flange 2 provides a multi-directional use for applying the stretchable material, ensuring a custom fit and secure seal around all facial characteristics. The wire face flange 2 can preferably be adjusted by bending it to accommodate certain facial features that may or may not be more prominent than the norm. This multi-directional movement of the wire face flange 2 allows the goggle to fit all faces with their unique characteristics. This wire face flange 2 also floats inside the goggle observing head and helmet movement without losing the stretchable material's seal to the surface of the user's face. The wire face flange 2 also works in conjunction with the stretchable interior seal material. The 4-way properties of the material allow for it to follow the wire face flange's range of movement during use. The Nitinol wire provides the ability for the face flange to move and float all while the goggle is secure to the helmet by the silicone suspension system. This provides the user with a goggle that does not get pushed around by the helmet. The use of Nitinol wire allows for less sealing material than modern goggles. By taking half the sealing material off the face (mainly off the forehead) the attached stretchable material to the wire face flange 2 allows a cooler and more comfortable seal. Modern goggles use as many as three layers of foam attached to a urethane structure that encompasses the face. The modern urethane structures sealing material is used to compress, wick up moisture and fill in the gaps of each individual, which can add up to a stuffy and uncomfortable goggle. The Nitinol wire face flange system with stretchable material drastically reduces the need for gap foam and foam overall. The Nitinol wire face flange design is a unique hanger type system for the stretchable material used to seal across the bridge of the nose. This hanger system acts much like the metal structure of a hammock, but upside down letting the stretchable material conform to the face. The Nitinol wire is designed to curve over the bridge of the nose. On each side of this curve are nose paddles attached to the Nitinol wire. Left and right of the nose paddles are the cheek paddles also attached to the Nitinol wire. These nose and cheek paddles are used to grip the stretchable material.

The third component of the present invention is the face flange paddles. Preferably, there are two nose paddles and two check paddles rotatably attached to the wire face flange 2.

Unlike the modern goggle where the sealing/face foam is glued on a predetermined facial designed urethane structure providing a fit by compressing reticulated foam onto the face. The current invention's stretchable material is attached to face flange paddles that rotate on the wire face flange 2 as the stretchable material conforms and seals across the user's face it provides a custom fit for each individual's face.

Attached to the wire face flange 2 are the face flange paddles. They hold the stretchable material that is used to seal the goggle to the face. These face flange paddles preferably use a hook and loop system (such as that sold under the trademark Velcro) to attach the stretchable material. Alternatively, adhesive material may be used. These face flange paddles attached to the stretchable material and wire face flange are able to rotate and slide along wire. When the goggle is put on the face the face flange paddles grip and rotate manipulating the stretchable material as it conforms to the face. The Nitinol wire face flange provides the tension and pressure to rotate the paddles and manipulate the stretchable material. The Nitinol wire face flange provides a consistent tension for a safe and secure fit to each face. The face flange paddles grip and rotate with the stretchable material to conform to the different characteristics of each person's face.

The fourth component of the present invention is a 4-way stretchable material that can be stretched and manipulated in multiple directions. This stretchable material is preferably a neoprene product covered with a 4-way stretch compatible loop material. This stretchable material is designed to attach to the face flange paddles by a Velcro system or adhesive. Once attached to the face flange paddles the stretchable material rotates with the paddles as the tension from the face flange wire manipulates the material across the facial characteristics of the user by the face flange wire's tension. This process contours the material for a custom fit providing a safe and secure seal from environmental elements. The stretchable material is also use to seal the interior space of the goggle between the wire face flange 2 and frame. This is to prevent environmental elements from entering causing damage or irritation to the eyes.

The stretchable material preferably has characteristics that allow for a comfortable 4-way multidirectional elasticity under use in wide range temperatures, with strength, durability, provides sealing from environmental elements (air, water, smoke, dust, mud, snow, sand, etc.), chemical resistance and other properties conducive for use with the goggle. Preferably, the stretchable material can be put on or taken off through use of a Velcro system. This provides the user the capability to clean or replace the interior stretchable material. In a preferred embodiment of the current invention, the stretchable material can start at 1.5 mm, and when manipulated provides a thin contouring seal securely across the nose and cheeks. This differs from the 4, 5, 6 mm, and more of sealing foam used in the modern goggle, which encompasses the nose, cheeks, and across the forehead. The modern goggle's sealing foam primarily functions to compress the foam around the facial characteristics filling in all gaps for a secure seal. This thick layer of foam is one of the reasons modern goggles are stuffy and uncomfortable, it also retains heat and moisture. The current invention's use of stretchable sealing material is quite the opposite. It takes a minimum amount of material to seal. By using this minimum layer approach you have a thin, gasket-type functional seal. The current invention's minimal use of sealing material retains less body heat and moisture over the thick seal and moisture wicking foam of the modern goggle. This provides for a cooler and dryer goggle.

The current invention is a total fitment system comprised of two apparatuses enabling a new goggle frame design to expand past the old modern goggle parameters. With new parameters to be determined the goggle frame now has many design options for all attributes related to but not limited to head and eye protection.

The apparatus of the present invention provides head and eye protection to the user and comprises two apparatuses, or four components:

$1^{st}$ Apparatus: $1^{st}$ Component
  a the first apparatus is used to suspend and seal the frame of a goggle to the helmet
  b a suspension apparatus connected to a goggle frame used to seat goggle to the exterior shell of the helmet's facial opening
  c a suspension apparatus connected to the goggle's upper frame section and side frame sections forming a barrier that suspends and seals the goggle frame to the exterior shell of the helmet as it conforms around the facial opening of helmet
  d the suspension apparatus connected to the goggle frame secures itself to the helmet's outer shell with the suspension's leading edge that extends rearward from goggle frame to engage along the contour of the helmet's facial openings outer shell
  e attached to a goggle frame the suspension apparatus provides multiple locations for the goggle to seat itself onto the outer shell of the helmet's facial opening
  f attached to a goggle frame the suspension apparatus provides the goggle frame the ability to absorb shock and movement while engaged to the outer shell of the helmet
  g attached to a goggle frame the suspension apparatus in conjunction with second apparatus allows the goggle frame to stay safely secure to the helmet and user's face as the helmet and head move during use
  h the attached suspension apparatus is preferably made of silicone material stays engaged to its seated position attributed to its design and the hot and cold flexibility temperature range of silicone
  i silicone suspension apparatus supplies the flexibility for the goggle frame to absorb shock and movement
  j silicone suspension apparatus supplies the compression needed to seat the leading edge of apparatus around the helmet's facial opening onto the exterior shell securing the goggle frame to the helmet k silicone suspension apparatus supplies the compression need to adjust the goggle frame within the proximity of the user's face using this as part of an overall fitment procedure to allow a custom safe and secure fit to any user's face l while silicone suspension apparatus's leading edge is engaged to the helmet this edge provides a seal preventing environmental elements from entering the goggle and disrupting the user's eyes providing a safe eye protection m use of silicone for the suspension apparatus provides load bearing capabilities for supporting the goggle frame with all its features not limited to including the lens, sealing material, straps, snap on parts, attachments and any other designed features integrated into the goggle 2nd Apparatus: 2nd Component a second apparatus is used to suspend and seal the frame of a goggle to the face b a suspension apparatus attached to a goggle frame used to seat the frame to the face of the user c a suspension apparatus attached to left and right side sections of the goggle's interior frame that suspends a wire face flange designed to go across the cheeks and nose of the face d attached to a goggle frame the wire face flange suspension apparatus is used to manipulate attached flexible material as it conforms across the cheeks and nose bridge of the user's face for a safe and secure seal e attached to a goggle frame the wire face flange suspension is preferably a Nitinol wire that provides the flexibility needed to adjust and seat the flexible material to any face f the wire face flange has multiple directional flexibility so each user can adjust the location of the initial engagement to fit their facial characteristics.

g the wire face flange provides the tension needed to manipulate the stretchable material across cheeks and nose bridge for a safe and secure seal h the wire face flange suspension characteristics provides the user with a safe and secure seal as the helmet and head move during use i the wire face flange acts as a structure used to hang flexible material used to seal environmental elements from getting into the eyes j the wire face flange is designed to have a measurable gap as it crosses over the bridge of the nose leaving room for the flexible material to manipulate, stretch and conform to the shape of the nose bridge k the wire face flange suspension in conjunction with the silicone suspension allows the face flange to float and keep the flexible material securely sealed to the user's face as the helmet and head move about during use l the wire face flange suspension provides the goggle the flexibility to have the multiple facial characteristics of the human face to be fitted m the wire face flange can have its wire bent to fit any unusual facial characteristics that may arise n the wire face flange is used to keep a consistent measured amount of tension on the flexible material to provide a safe and secure seal across the cheeks and nose 2nd Apparatus: 3rd Component a this component consists of a set of paddles that are used to suspend the flexible material from the wire face flange b these paddles attach to the wire face flange, preferably comprising one left cheek paddle, one right cheek paddle, and two nose paddles, one on each side of the nose; each paddle rotates separately on the wire face flange c each paddle securely holds the flexible material so the wire face flange can rotate the paddles while they manipulate the flexible material to contour across the cheeks and nose for a secure seal d the rotation of each paddle stretches and manipulates the attached flexible fabric as the wire face flange applies the tension e the paddles provide a platform to secure the flexible material so the tension from the wire face flange will rotate the attached paddles causing the flexible material to be manipulated and conform across the cheeks and nose bridge of the user's face 2nd Apparatus: 4th Component a this component is the flexible material used to seal the goggle frame to the face b at the designed location this flexible material provides the goggle with a seal preventing environmental elements from getting into the eyes creating irritation or damage c the flexible material has four-way stretch, lending itself to be manipulated into place and form a safe and secure seal d the stretchable material can be permanently attached or, preferably use a Velcro or other reusable adhesive system so it can be replaced or removed to clean e the flexible material provides for a cooler and dryer goggle from the heat and sweat produced by the user's face during use this due to the flexible materials thin layer used for sealing off the environmental elements reducing the amount of heat retained lessening the sweat produced f the flexible material can be permanently attached, or preferably use a Velcro or other reusable adhesive system to attach itself along multiple designed attachment locations across the wire face flange and around the interior of the goggle frame along with the attached lens to provide a safe and secure seal preventing the environmental elements from entering the interior space of the goggle protecting the eyes The following is a list of parts and materials suitable for use in the present invention.

PARTS LIST AND DIRECTIONAL INFORMATION

Part Number Description
1 Frame/Helmet apparatus system
2 Frame/Face apparatus system
3 Helmet outer shell
4 Silicone Suspension leading edge
5 Silicone Suspension
6 Goggle frame
7 Silicone Suspension's directional seating options
8 Silicone Suspension's multiple up and down seating points
9 Wire Face Flange
10 Wire Face Flange's multi direction flexibility
11 Nose Paddles 12 Cheek Paddles
13 Nose Paddles directional movement
14 Cheek Paddles directional movement
15 Directional movement of stretchable material around nose
16 Directional movement of stretchable material around cheeks
17 Face Flange's stretchable material
18 Stretchable facial comfort material
19 Vent foam filter
20 Stretchable interior seal material
21 Directional movement of stretchable interior seal material.
23 Attachment locations for interior seal material All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A head and eye protection apparatus comprising:
a) a helmet that is shaped to envelope a wearer's head, the helmet having a front viewing opening that enables the wearer to see;
b) the helmet having a helmet outer surface, an upper edge and left and right side edges that are next to the front viewing opening;
c) a goggle, the goggle having a transparent viewing lens supported by a peripheral frame, said frame including an upper frame section, left and right side frame sections, and a lower frame section;
d) a first suspension component that connects the goggle to the helmet at the front viewing opening, the first suspension component having a leading edge that extends rearward from the goggle frame, and suspends the goggle frame from the helmet outer surface upper edge;
e) a second suspension component for connecting the goggle to a wearer's face, the second suspension component having a flexible face flange that connects to the left and right side goggle frame sections, and is sized and shaped to engage cheeks and nose bridge of the wearer;
f) a plurality of paddles sized and shaped for engaging the wearer's face, the paddles being connected to the flexible face flange of the second suspension component; and,
g) a first flexible material for connecting the goggle frame to the wearer's face, the first flexible material sized and shaped to create a seal between the goggle frame and forehead, temples, and sides of the wearer's face.

2. The apparatus of claim 1, wherein the first suspension component also seals the goggle frame to the helmet outer surface at the upper edge and left and right side edges.

3. The apparatus of claim 1, wherein the first suspension component provides a plurality of attachment points between the goggle frame and the outer surface of the helmet.

4. The apparatus of claim 1, wherein the first suspension component is made of silicone material.

5. The apparatus of claim 1, wherein the flexible face flange of the second suspension component is shaped to provide a measurable indentation where it crosses the wearer's nose bridge when worn by the wearer, the indentation being filled with a second flexible material for conforming to the shape of the wearer's nose bridge.

6. The apparatus of claim 5, wherein the first and second flexible material is between 1 and 4 mm thick.

7. The apparatus of claim 5, wherein the first and second flexible material is between 1.5 and 2.0 mm thick.

8. The apparatus of claim 5, wherein the flexible face flange of the second suspension component has multi-directional flexibility and keeps a consistent, measured amount of tension on the second flexible material.

9. The apparatus of claim 1, wherein the flexible face flange of the second suspension component is composed of Nitinol wire.

10. The apparatus of claim 1, wherein there are at least two paddles that rotate separately on the flexible face flange, including a left cheek paddle and a right cheek paddle.

11. The apparatus of claim 1, wherein there are at least four paddles that rotate separately on the flexible face flange, including a left cheek paddle, a right cheek paddle, and two nose paddles, one of the nose paddles corresponding to the left side of the wearer's nose bridge and the other nose paddle corresponding to the right side of the wearer's nose bridge.

12. The apparatus of claim 1, wherein the first flexible material is permanently attached to the goggle frame.

13. The apparatus of claim 1, wherein the first flexible material is attached to the goggle frame using a reusable adhesive system.

14. The apparatus of claim 13, wherein the reusable adhesive system is a hook and loop fastener system.

15. The apparatus of claim 1, wherein the first flexible material is between 1 and 4 mm thick.

16. The apparatus of claim 1, wherein the first flexible material is between 1.5 and 2.0 mm thick.

17. The apparatus of claim 1, wherein said face flange is a flexible multidirectional face flange.

* * * * *